US010765512B2

(12) United States Patent
Rylski et al.

(10) Patent No.: US 10,765,512 B2
(45) Date of Patent: Sep. 8, 2020

(54) CARDIAC REPAIR PROSTHESIS SETS AND METHODS

(71) Applicant: The Trustees Of The University Of Pennsylvania, Philadelphia, PA (US)

(72) Inventors: Bartosz Rylski, Philadelphia, PA (US); Joseph Bavaria, Philadelphia, PA (US); Rita Carrie Milewski, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 13 days.

(21) Appl. No.: 15/829,190

(22) Filed: Dec. 1, 2017

(65) Prior Publication Data

US 2018/0110615 A1 Apr. 26, 2018

Related U.S. Application Data

(63) Continuation of application No. 14/334,096, filed on Jul. 17, 2014, now Pat. No. 9,861,474.
(Continued)

(51) Int. Cl.
*A61F 2/24* (2006.01)
*A61F 2/07* (2013.01)
(Continued)

(52) U.S. Cl.
CPC .......... *A61F 2/2412* (2013.01); *A61B 17/122* (2013.01); *A61B 17/128* (2013.01);
(Continued)

(58) Field of Classification Search
CPC ........ A61F 2/24; A61F 2/2412; A61F 2/2418; A61F 2/942
(Continued)

(56) References Cited

U.S. PATENT DOCUMENTS 4,086,665 A * 5/1978 Poirier ...................... A61F 2/06
138/109
6,102,845 A * 8/2000 Woodard ............ A61M 1/3659
600/16
(Continued)

FOREIGN PATENT DOCUMENTS

| WO | 95/03754 A1 | 2/1995 |
| WO | 2010/011736 A1 | 1/2010 |
| WO | 2013/078497 A1 | 6/2013 |

OTHER PUBLICATIONS

Wheatley, "Marching Closer Toward a Convergence of Technologies for Thoracic Arotic Endografting and Percutaneous Heart Valve Therapies", J. Endovasc. Ther., Jun. 2011, 18, 357-358.

*Primary Examiner* — Suzette J Gherbi
(74) *Attorney, Agent, or Firm* — BakerHostetler

(57) ABSTRACT

Cardiac repair prostheses, sets, and methods for implanting in an aorta are disclosed. Cardiac repair prosthesis sets can include a radially expandable support supporting a unidirectional valve that is configured for implantation into the aortic valve region of a patient and a second radially expandable support for a substantially blood impervious stent having a size and shape for implantation into the ascending aorta of said patient where the unidirectional valve and stent are configured for integration within the patient by at least one joining element. Cardiac repair prostheses can include a radially expandable support supporting a unidirectional valve configured for implantation into the aortic valve region of a patient and a second radially expandable support for a substantially blood impervious stent having a size and shape for implantation into the ascending aorta of said patient where the unidirectional valve and stent are joined by at least one joining element.

14 Claims, 6 Drawing Sheets

Related U.S. Application Data

(60) Provisional application No. 61/847,879, filed on Jul. 18, 2013.

(51) Int. Cl.
*A61B 17/122* (2006.01)
*A61B 17/128* (2006.01)
*A61F 2/89* (2013.01)

(52) U.S. Cl.
CPC ............ *A61F 2/07* (2013.01); *A61F 2/2418* (2013.01); *A61F 2/89* (2013.01); *A61F 2220/0025* (2013.01); *A61F 2220/0075* (2013.01); *A61F 2220/0091* (2013.01); *A61F 2250/0097* (2013.01)

(58) Field of Classification Search
USPC .................................................. 623/2.1–2.19
See application file for complete search history.

(56) References Cited

U.S. PATENT DOCUMENTS

| | | | |
|---|---|---|---|
| 6,245,102 | B1 | 6/2001 | Jayaraman |
| 6,482,228 | B1 * | 11/2002 | Norred ............... A61F 2/2412 623/2.17 |
| 7,972,378 | B2 | 7/2011 | Tabor et al. |
| 8,715,337 | B2 * | 5/2014 | Chuter ................. A61F 2/07 623/2.1 |
| 9,289,282 | B2 * | 3/2016 | Olson ................... A61F 2/07 |
| 9,585,748 | B2 | 3/2017 | Wright |
| 2001/0021872 | A1 | 9/2001 | Bailey et al. |
| 2005/0222674 | A1 * | 10/2005 | Paine ................... A61F 2/07 623/1.24 |
| 2009/0171457 | A1 | 7/2009 | Song |
| 2012/0283820 | A1 | 11/2012 | Tseng et al. |
| 2013/0013051 | A1 | 1/2013 | Benary |
| 2013/0204343 | A1 | 8/2013 | Shalev |
| 2016/0030209 | A1 | 2/2016 | Shalev et al. |
| 2016/0081829 | A1 * | 3/2016 | Rowe .................. A61F 2/2412 623/1.12 |
| 2016/0193029 | A1 | 7/2016 | Shalev |

* cited by examiner

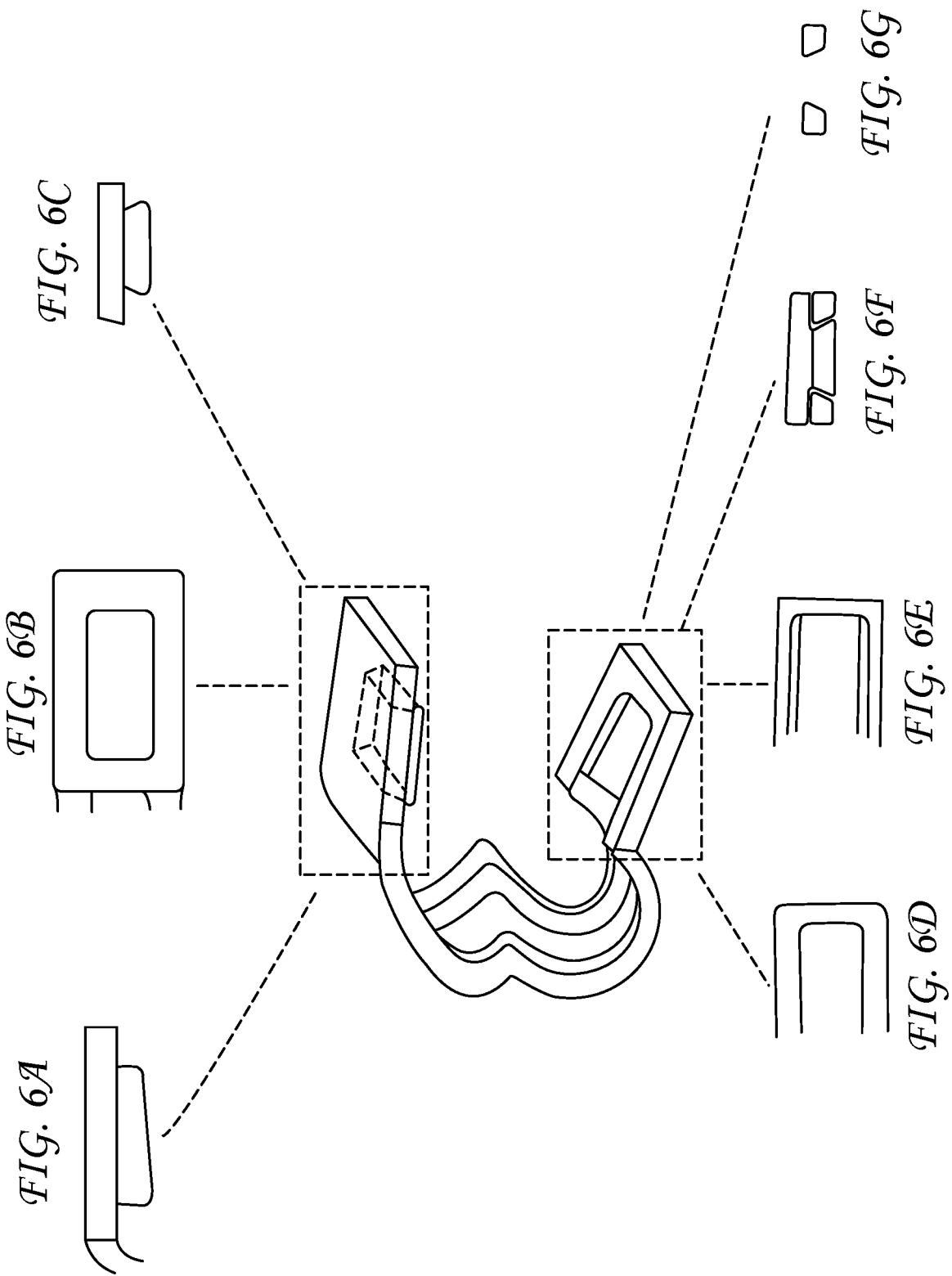

CARDIAC REPAIR PROSTHESIS SETS AND METHODS

CROSS-REFERENCE TO RELATED APPLICATIONS

The present application is a continuation of U.S. Ser. No. 14/334,096, filed on Jul. 17, 2014, which claims priority to U.S. Provisional App. No. 61/847,879, filed Jul. 18, 2013, the entire contents of both of which are hereby incorporated by reference.

TECHNICAL FIELD

The invention generally relates to medical devices for the endovascular treatment of ascending aortic and aortic valve diseases.

BACKGROUND

Patients with aortic valve disease and ascending aortic dilation have two separate, but interrelated disease processes which require surgical replacement or repair. In these patients, replacement or repair of the valve without therapeutic intervention on the dilated aorta condemns the patient to catastrophic lethal events such as aortic dissection or rupture. Likewise, therapeutic intervention of the ascending aorta without repair or replacement of the stenotic or regurgitant aortic valve leaves the patient with symptomatic shortness of breath, heart failure, and eventual death.

Patients with aortic valve disease who are at high risk for classic open aortic valve replacement are offered a minimal-invasive treatment option—transcatheter aortic valve replacement (TAVI). A current contraindication for TAVI is concomitant ascending aortic ectasia/aneurysm. There are two potential disadvantages of isolated TAVI in patients with concomitant ascending aorta dilatation. First, TAVI which requires intra-aortic manipulation utilizing wires, catheters, and deployment devices can result in catastrophic outcomes such as acute aortic dissection or rupture of the diseased, dilated ascending aorta. Second, as mentioned, patients with aortic valve disease and ascending aortic dilatation have high risk of spontaneous aortic dissection or rupture. TAVI treatment for aortic valve disease in patients with concomitant ascending aortic dilatation does not eliminate the risk of catastrophic aortic events such as aortic dissection and aortic rupture.

Above-mentioned reasons show why it is essential to replace both the dilated ascending aorta and diseased aortic valve simultaneously. Since completing TAVI with endovascular ascending aortic repair is still challenging and not well established, these patients despite their high risk for cardiac surgery undergo open surgery or continue medical treatment only.

It is the objective of this invention to provide a single device for minimally invasive treatment of both aortic valve and ascending aortic disease in a one-stage procedure.

SUMMARY

Cardiac repair prosthesis sets and cardiac repair prostheses are disclosed. A cardiac repair prosthesis set can include a radially expandable support supporting a unidirectional valve that is configured for implantation into the aortic valve region of a patient and a second radially expandable support for a substantially blood impervious stent having a size and shape for implantation into the ascending aorta of said patient where the unidirectional valve and stent are configured for integration within the patient by at least one joining element.

In another embodiment, a kit for bioimplantable aortic valve and ascending aortic stent assemblies can include a plurality of implantable aortic valves in at least two different sizes or conformations; a plurality of implantable stents having a size and conformation suitable for implantation into the ascending aorta in at least two different sizes or conformations; and, optionally, material for fastening an aortic valve to an aortic stent prior to implantation.

A cardiac repair prosthesis can include a radially expandable support supporting a unidirectional valve configured for implantation into the aortic valve region of a patient and a second radially expandable support for a substantially blood impervious stent having a size and shape for implantation into the ascending aorta of said patient where the unidirectional valve and stent are joined by at least one joining element.

The invention also relates to methods for implanting a cardiac repair prosthesis. In an embodiment of such a method the cardiac repair prosthesis can include a radially expandable support supporting a unidirectional valve and a second radially expandable support for a substantially blood impervious stent having a size and shape for implantation into the ascending aorta of said patient where the unidirectional valve and stent are joined by at least one joining element. In such an embodiment a method for implanting a cardiac repair prosthesis can include the step of positioning the first radially expandable support in the aortic valve region aorta of a patient so that the first radially expandable support is secured in the aortic annulus of the patient.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings.

Figure 1:
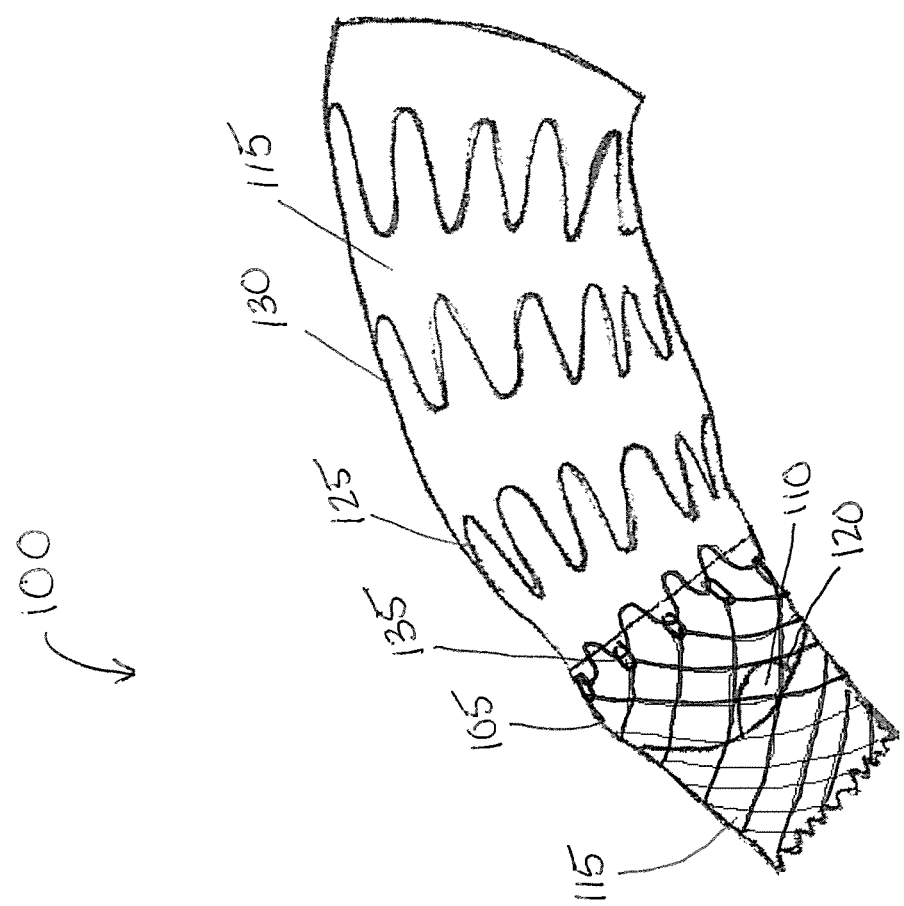
FIG. 1 is a side view of an embodiment of the invention.

As described more fully below, FIGS. 6A-G provide perspective views of a joining element of an embodiment of the invention.

FIG. 6A is an exploded side view of a positive lock portion of a joining element of an embodiment of the invention.

FIG. 6B is an exploded bottom view of a positive lock portion of a joining element of an embodiment of the invention.

FIG. 6C is an exploded top view of a positive lock portion of a joining element of an embodiment of the invention.

FIG. 6D is an exploded top view of a negative lock portion of a joining element of an embodiment of the invention.

FIG. 6E is an exploded bottom view of a negative lock portion of a joining element of an embodiment of the invention.

FIG. 6F is an exploded side view of a positive lock portion and a negative lock portion of a joining element in a locked position; and FIG. 6G is an exploded side view of a cut-away of a negative lock portion of a joining element of an embodiment of the invention.

DETAILED DESCRIPTION OF ILLUSTRATIVE EMBODIMENTS

The present invention may be understood more readily by reference to the following description taken in connection with the accompanying Figures, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the features and methods of making and using cardiac repair prostheses and sets, as well as the cardiac repair prostheses and sets themselves, and vice versa.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Referring to FIG. 1, a cardiac repair prosthesis 100 can include a radially expandable support 105 supporting a unidirectional valve 110. The radially expandable support 105 can be made of struts, mesh, or other scaffolding and may be partially covered with a material 115 that is substantially impermeable to blood, such as porcine or bovine pericardial tissue, or Dacron material. As used herein in the term covered in reference to a radially expandable support can refer to a material that surrounds the outside of the support, the inside of the support, or is integral with the support. The unidirectional valve can be any type of valve that serves to form a seal against the flow of fluid in one direction, but allows the flow of fluid in an opposing direction. Preferred valves include one or more leaflets 120, such as two leaflets or three leaflets, that can mimic the function of leaflets in a healthy human aortic valve. Leaflets can be made of biological material or of synthetic material. Example combinations of radially expandable support and unidirectional valves are replacement valves that are used in transcatheter aortic valve replacement procedures such as the Corevalve by Medtronic or Sapien by Edwards Lifesciences. Any type of unidirectional valve known to a person of skill in the art that can be collapsed to be delivered through an artery, ventricle, or otherwise endovascularly, and expanded when positioned within an aorta can be used. The radially expandable support supporting a unidirectional valve can be configured for implantation into the aortic valve region of a patient. For example, the radially expandable support can be secured in the aortic annulus of a patient. Calcification of a damaged aortic annulus can be useful in securing the radially expandable support in the aortic annulus.

Still referring to FIG. 1, a cardiac repair prosthesis 100 can further include a second radially expandable support 125 for a substantially blood impervious stent 130 having a size and shape for implantation into the ascending aorta of a patient. The second radially expandable support 125 can be made of struts, mesh, or other scaffolding and can be at least partially covered with a material 115 that is substantially impermeable to blood, such as Dacron material. The second radially expandable support can have a length and a circumference and can be covered with a material 115 that is substantially impervious to blood both along the length of the second radially expandable support and around the circumference of the second radially expandable support. In preferred embodiments, a portion of the second radially expandable support is covered that corresponds to the portion that would extend from the sinotubular junction past the dilated portion of the ascending aorta in a patient. Such a covering allows blood to flow solely through the stent, eliminating the stress of high arterial blood pressure on the ascending aortic wall. In some embodiments the entire length and circumference of the second expandable support can be covered, so long as when implanted in a patient the second expandable support and covering do not extend below the sinotubular junction and impede blood flow to the coronary arteries. In other embodiments a portion of the second expandable support is uncovered so that when implanted in a patient the uncovered portion extends from the sinotubular junction of the patient's aorta into the aortic sinus and does not impede the flow of blood to the coronary arteries. That is, in some embodiments the second radially expandable support can extend beyond the substantially blood impervious stent and in other embodiments the second radially expandable support and the substantially blood impervious stent can be substantially equal in length. The length, collapsed diameter, and expanded diameter of the second radially expandable scaffolding will depend on the size and shape of the aorta of the patient being treated where the collapsed diameter refers to the diameter of the second radially expandable support before being expanded and the expanded diameter refers to the diameter of the second radially expandable support after being expanded. Moreover, the size of the stent can be chosen to have a proximal diameter that is different from the distal diameter, that is the diameter at one end of the stent can differ from the diameter of the opposite end of the stent, in order to best fit the anatomy of the patient to be treated. The length of the substantially blood impervious stent is preferably long enough to span the length of the damaged area of the ascending aorta of the patient to be treated and extend beyond the damaged area a sufficient length to create a seal between the stent and the sinotubular junction and the ascending aorta, preventing blood flow from passing against the damaged area of the ascending aorta. For example, the length of the landing zone can be from about 5 mm to about 10 mm. For example, the length of the covered portion can be in the range of from about 5 cm to about 8 cm, or any length suitable to treat a patient. The length of the expanded support can be longer than the length of the stent, as in the case where the expanded support is long enough to extend into the aortic sinus of the patient and a portion of the expanded support is uncovered so as to allow blood to freely flow to the coronary arteries. The length of the expanded support can be in a range from about 7 cm to about 10 cm, or any length suitable to treat a patient.

In a cardiac repair prosthesis as shown in FIG. 1, the unidirectional valve and stent can be joined by at least one joining element 135, and preferably more than three joining elements 135, such as about 4 to about 6 joining elements. That is, the first expandable scaffolding and the second expandable scaffolding can be joined by at least one joining element 135 so that the radially expandable support 105 support for supporting a unidirectional valve 110 and the second radially expandable support for a substantially blood impervious stent 130 are connected to form a single cardiac repair prosthesis 100 that can be implanted in a single procedure. Such a connection can be referred to herein as a frame-to-frame connection. A joining element 135 can be any connector that is biocompatible and can hold the second expandable scaffolding adjacent to the first expandable scaffolding so that when the first expandable scaffolding is secured in the aortic annulus of a patient, the second expandable scaffolding will also be secured in the ascending aorta because it is tethered to the first expandable scaffolding. Example joining elements can be a suture or a clip. A suture can be made using any thread or material known to make a suitable suture, including but not limited to Mersilene, Ethilon, or Ethibond made by Ethicon. A clip can be made of plastic, metal, or any biocompatible material including, but not limited to stainless steel, titanium, or a combination thereof.

Figure 2:
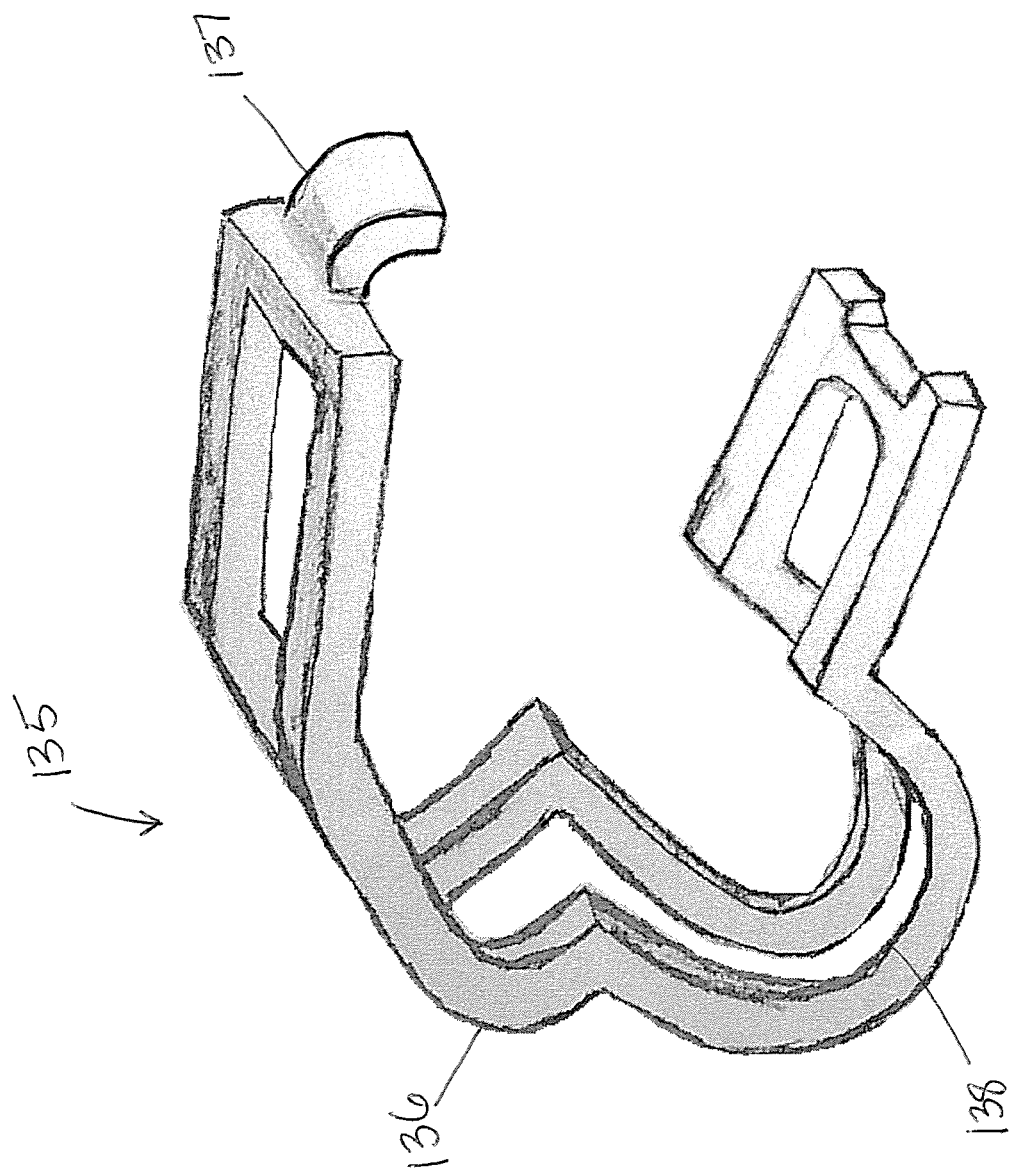
FIG. 2 is a perspective view of a joining element of an embodiment of the invention.
Figure 3B:
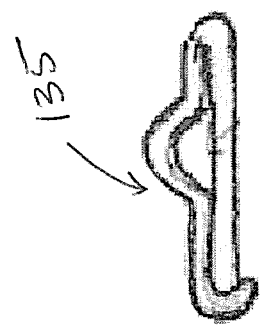
FIG. 3b is a side view of a joining element of an embodiment of the invention in a closed position.
Figure 3A:
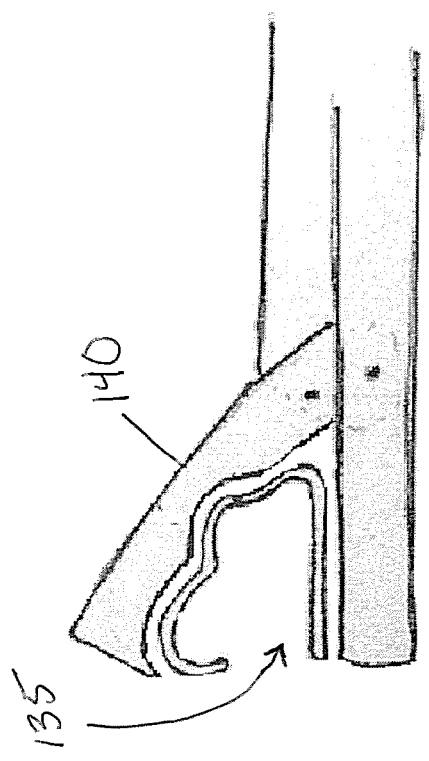
FIG. 3a is a side view of a joining element of an embodiment of the invention in an open position.
Figure 4:
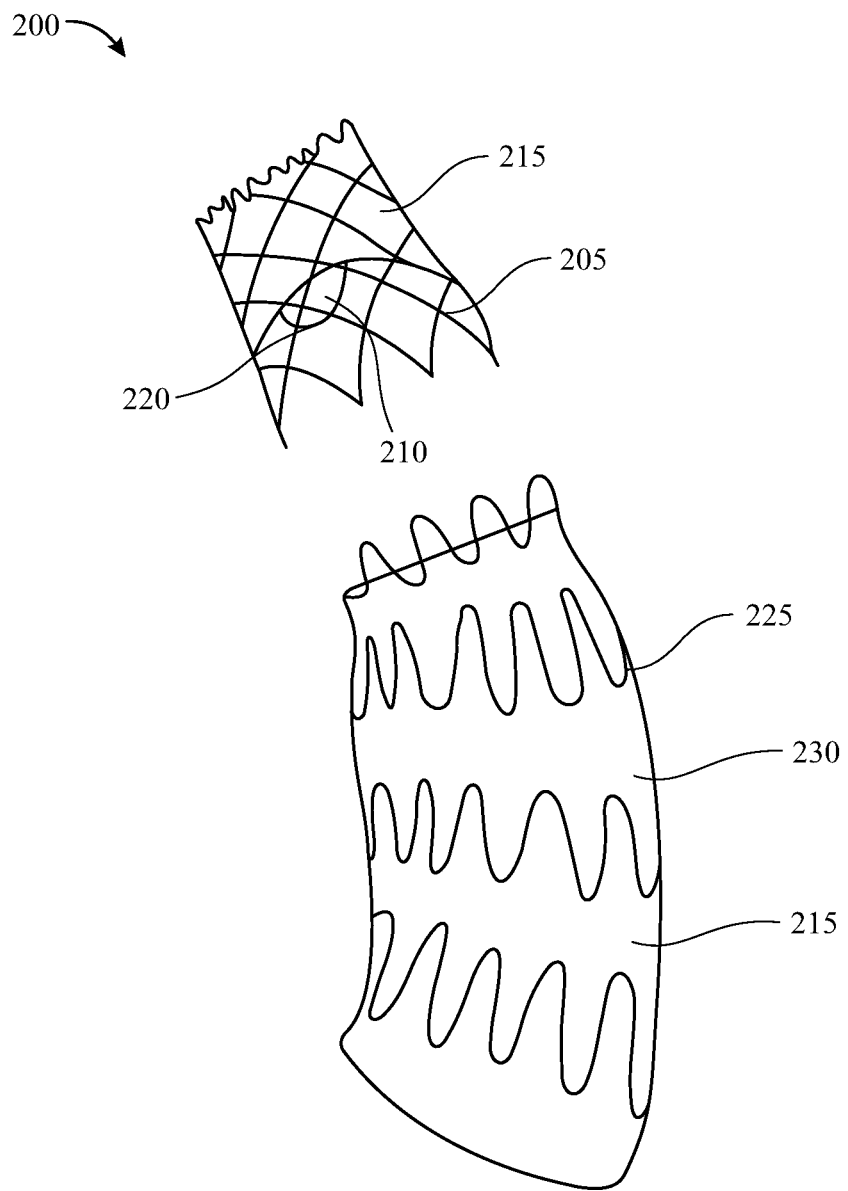
FIG. 4 is a side view of an embodiment of the invention.

Referring now to FIGS. 2-4, a joining element 135 useful with the present invention can include a hinge 136 and a lock 137. A hinge can allow the joining element to be opened and closed around the first and second radially expandable scaffolds. A lock can prevent opening of the clip and twisting of the clip. A joining element 135 can also include a slot 138 that provides a space for a portion of both the valve and the stent, or a portion of both the first and second radially expandable scaffolds, to fit within the joining element when the joining element 135 is in a closed position. FIG. 3A illustrates a joining element 135 in an open position, together with a device 140 for locking the joining element 135 closed. FIG. 3B illustrates a joining element 135 in a closed or locked position. FIGS. 6A-6G illustrate a joining element having an alternative locking feature having a positive locking portion 138 and a negative locking portion 139.

Cardiac repair prosthesis of the invention can be made using conventional transcatheter aortic valve replacement prostheses and a stent specially shaped and fitted for the ascending aorta of the patient to be treated. A medical professional can connect the two pieces, such as in a frame-to-frame connection using a suture or a specially designed clip. Alternatively, cardiac repair prostheses of the invention can be made at a remote location by joining a transcatheter aortic valve and a stent, such as with a suture or a clip. Because of the modular nature of the prosthesis, each prosthesis can be custom sized to a patient's anatomy.

In another embodiment, the invention provides for kits for bioimplantable aortic valve and ascending aortic stent assemblies. Such kits can include a plurality of implantable aortic valves in at least two different sizes or conformations; a plurality of implantable stents having a size and conformation suitable for implantation into the ascending aorta in at least two different sizes or conformations; and, optionally, material for fastening an aortic valve to an aortic stent prior to implantation. Implantable aortic valves can be any type of unidirectional valve described above. Implantable stents can be any type of stent sized and shaped to fit a patient's ascending aorta, as described above. In embodiments where a kit includes a material for fastening an aortic valve to an aortic stent prior to implantation, the material can comprise a biocompatible clip as described above, or a suturing material, examples of which have been described above. Alternatively, a kit can include aortic valves and stents that are designed to self-entangle. That is either the aortic valves or the stents (or both) can have hooks that are designed to be used to connect to the other of the stents or the aortic valves.

In another embodiment, and referring to FIG. 4, the invention provides for a cardiac repair prosthesis set 200 that can include a radially expandable support 205 supporting a unidirectional valve 210 that is configured for implantation into the aortic valve region of a patient. The radially expandable support 205 can be made of struts, mesh, or other scaffolding and may be partially covered with a material 215 that is substantially impermeable to blood, such as porcine or bovine pericardial tissue, or Dacron material. As used herein in the term covered in reference to a radially expandable support can refer to a material that surrounds the outside of the support, the inside of the support, or is integral with the support. The unidirectional valve can be any type of valve that serves to form a seal against the flow of fluid in one direction, but allows the flow of fluid in an opposing direction. Preferred valves include one or more leaflets 220, such as two leaflets or three leaflets, that can mimic the function of leaflets in a healthy human aortic valve. Example valves are valves that are used in transcatheter aortic valve replacement procedures such as the Corevalve by Medtronic or Sapien by Edwards Lifesciences. Any type of unidirectional valve known to a person of skill in the art that can be collapsed to be delivered through an artery, ventricle, or otherwise endovascularly, and expanded when positioned within an aorta can be used. The radially expandable support supporting a unidirectional valve can be configured for implantation into the aortic valve region of a patient. For example, the radially expandable support can be secured in the aortic annulus of a patient. Calcification of a damaged aortic annulus can be useful in securing the radially expandable support in the aortic annulus.

Still referring to FIG. 4, a cardiac repair prosthesis set 200 can further include a second radially expandable support 225 for a substantially blood impervious stent 230 having a size and shape for implantation into the ascending aorta of a patient. The second radially expandable support 225 can be made of struts, mesh, or other scaffolding and can be at least partially covered with a material 215 that is substantially impermeable to blood, such as Dacron. The second radially expandable support can have a length and a circumference and can be covered with a material 215 that is substantially impervious to blood both along the length of the second radially expandable support and around the circumference of the second radially expandable support. In preferred embodiments, a portion of the second radially expandable support is covered that corresponds to the portion that would extend from the sinotubular junction past the dilated portion of the ascending aorta in a patient. Such a covering allows blood to flow through solely the stent, eliminating the stress of high arterial blood pressure on the ascending aortic wall. In some embodiments the entire length and circumference of the second expandable support can be covered, so long as when implanted in a patient the second expandable support and covering do not extend below the sinotubular junction and impede blood flow to the coronary arteries. In other embodiments a portion of the second expandable support is uncovered so that when implanted in a patient the uncovered portion extends from the sinotubular junction of the patient's aorta into the aortic sinus and does not impede the flow of blood to the coronary arteries. That is, in some embodiments the second radially expandable support can extend beyond the substantially blood impervious stent and in other embodiments the second radially expandable support and the substantially blood impervious stent can be substantially equal in length. The length, collapsed diameter, and expanded diameter of the second radially expandable scaffolding will depend on the size and shape of the aorta of the patient being treated where the collapsed diameter refers to the diameter of the second radially expandable support before being expanded and the expanded diameter refers to the diameter of the second radially expandable support after being expanded. Moreover, the size of the stent can be chosen to have a proximal diameter that is different from the proximal diameter, that is the diameter at one end of the stent can differ from the diameter of the opposite end of the stent, in order to best fit the anatomy of the patient to be treated. The length of the substantially blood impervious stent is preferably long enough to span the length of the damaged area of the ascending aorta of the patient to be treated and extend beyond the damaged area a sufficient length to create a seal between the stent and the and the sinotubular junction and the ascending aorta, preventing blood flow from passing against the damaged area of the ascending aorta. For example, the length of the landing zone can be from about 5 mm to about 10 mm. For example, the length of the covered portion can be in the range of from about 5 cm to about 8 cm, or any length suitable to treat a patient. The length of the expanded support can be longer than the length of the stent, as in the case where the expanded support is long enough to extend into the aortic sinus of the patient and a portion of the expanded support is uncovered so as to allow blood to freely flow to the coronary arteries. The length of the expanded support can be in a range from about 7 cm to about 10 cm, or any length suitable to treat a patient.

In a cardiac repair prosthesis set as shown in FIG. 4, the unidirectional valve and stent can be configured for integration within the patient by at least one joining element 235. That is, the first expandable scaffolding and the second expandable scaffolding are designed to be joined together using at least one joining element 235 so that the radially expandable support 205 support supporting a unidirectional valve 210 and the second radially expandable support for a substantially blood impervious stent 230 are connected to form a single cardiac repair prosthesis, such as described in another embodiment, that can be implanted in a single procedure. For example, the first and second radially expandable supports may each have a portion that is not covered, leaving the support structure exposed; the support structures can be joined using one or more joining elements. Such a connection between the first and second radially expandable supports can be referred to herein as a frame-to-frame connection. The first and second radially expandable supports can be integrated before implanting into a patient so that the cardiac repair prosthesis set can be delivered into a patient in a single procedure. Cardiac repair prosthesis sets of the invention may optionally include one or more joining elements. Alternatively, a joining element such as a suture may be used with a cardiac repair prosthesis set and is not necessary to include in the cardiac repair prosthesis set. Examples of joining elements that may be included as part of a cardiac repair prosthesis include any connector that is biocompatible and can hold the second expandable scaffolding adjacent to the first expandable scaffolding so that when the first expandable scaffolding is secured in the aortic annulus of a patient, the second expandable scaffolding will also be secured in the ascending aorta because it is tethered to the first expandable scaffolding. Example joining elements can be a suture or a clip. A clip can be made of plastic, metal, or any biocompatible material including, but not limited to stainless steel, titanium, or a combination thereof. In some embodiments, the joining elements shown in FIGS. 2-3 and described with respect to the cardiac prosthesis embodiments above can also be included in the cardiac prosthesis set.

Apparatuses of the invention can be used to repair aortic valve and ascending aorta in a patient. In some embodiments methods for repairing aortic valve and ascending aorta use a cardiac repair prosthesis comprising a radially expandable support supporting a unidirectional valve and a second radially expandable support for a substantially blood impervious stent having a size and shape for implantation into the ascending aorta of said patient, the unidirectional valve and stent being joined by at least one joining element. Methods for repairing aortic valve and ascending aorta can include the step of positioning the first radially expandable support in the aortic valve region aorta of a patient so that the first radially expandable support is secured in the aortic annulus of the patient. In some embodiments the method can further include positioning the second radially expandable support so that a portion of the second radially expandable support is flush with the interior wall of the aorta at the sinotubular junction of the patient. A cardiac repair prosthesis can be delivered to the aorta either through a femoral artery, through a left ventricle or in any other manner that can be used in TAVI, as will be understood by a person of skill in such procedures. A guidewire can be inserted through the chosen point of entry and a catheter that has been loaded with a cardiac repair prosthesis can be inserted along the guidewire to the site of implantation. Each radially expandable support can independently be expanded using a balloon or can be self-expanded.

Figure 5:
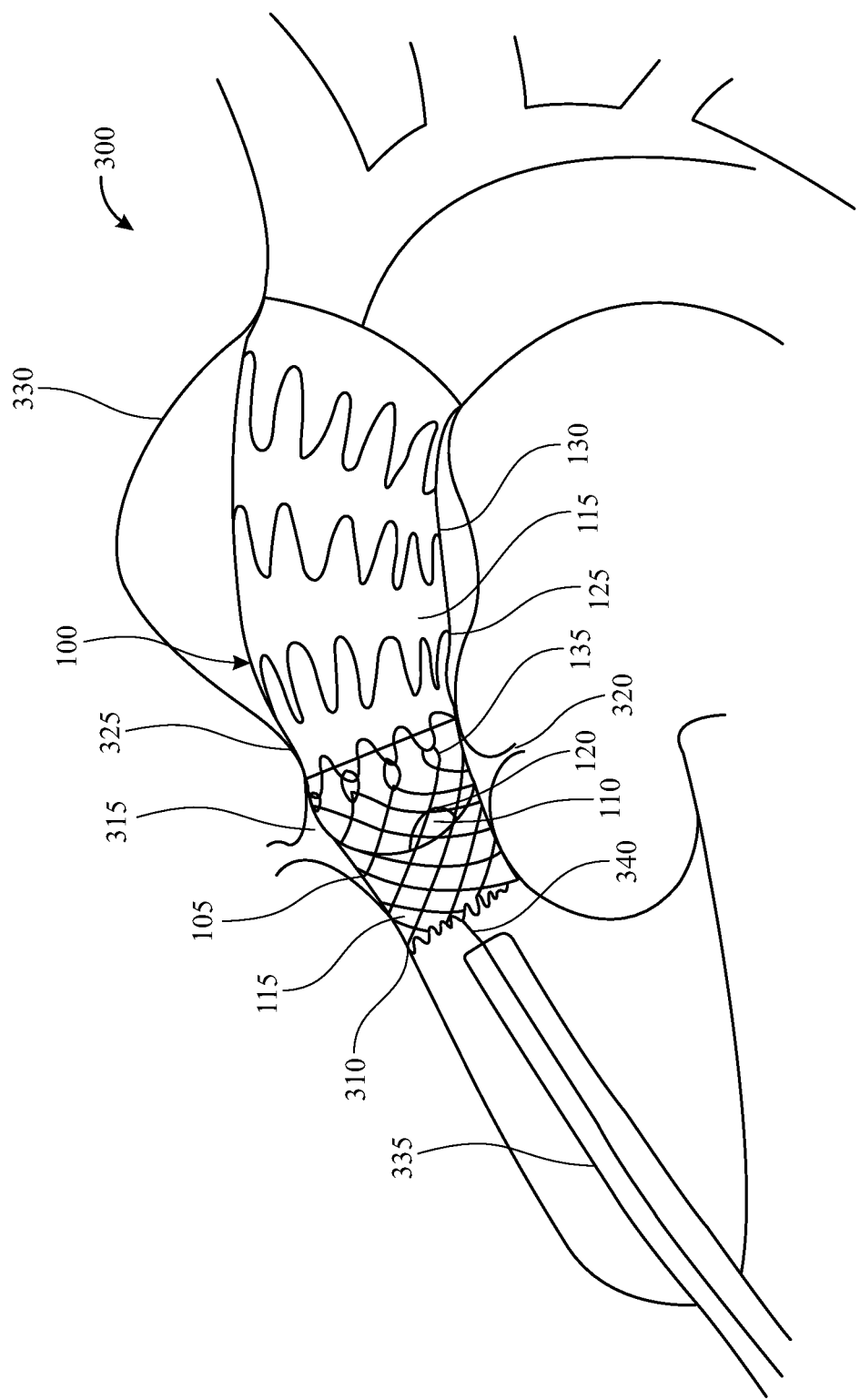
FIG. 5 is a side view of an embodiment of the invention positioned within an aorta.

FIG. 5 illustrates an embodiment of the invention implanted in an aorta 300 of a patient. The first radially expandable support supporting a unidirectional valve can be implanted in the aortic annulus 310. The first radially expandable support can be secured in the aortic annulus by expanding the radially expandable support into the aortic annulus. The portion of the first radially expandable support extending through the aortic sinus 315 is preferably uncovered to allow blood to freely flow to the coronary arteries 320 in the diastolic phase. In an alternative embodiment not shown, an uncovered portion of the second radially expandable support can extend below the sinotubular junction 325 into the aortic sinus. The second radially expandable support can be covered at least over a portion that extends from the sinotubular junction 325 beyond the dilated or damaged portion of the ascending aorta 330. Damage to the ascending aorta can include dilation or aneurysm. A cardiac prosthetic device can be delivered to the aorta on a catheter 335 that travels along a guidewire 340.

Additional Disclosure

Methods of the invention can be referred to as a one-stage endovascular Wheat-type procedure. A Wheat procedure is a cardiac surgery operation consisting of aortic valve and supra-coronary ascending aortic replacement with preservation of the sinus of Valsalva. The endovascular Wheat procedure of the present invention is a novel an endovascular replacement of both aortic valve and ascending aorta with free diastolic blood flow to the sinus segment and coronary arteries. This endovascular Wheat procedure recapitulates the surgical concept of Wheat supracoronary ascending aortic approach. This concept is to maintain the coronary arteries intact with physiologic diastolic flow to the native coronary arteries.

TAVI enables endovascular aortic valve replacement. Although endovascular techniques are available for the transverse and descending thoracic aorta, one main limitation for endovascular approach to the dilated ascending aorta is the lack of appropriate proximal landing zone. The landing zone in endovascular aortic replacement is a segment of normal aorta which is utilized to securely seal the device to the aorta wall and prevent stent migration. Physiologically, the proximal landing zone in the dilated ascending aorta is the sinotubular junction. This region, which is anatomically only a few millimeters is not an appropriate length for an endovascular landing zone. The length of the native sinotubular junction cannot be altered and nor are there any current intraluminal methods to extend this landing zone. An advantage of medical devices of the invention is that these device have a novel, very stable and proven landing zone. These devices have a proximal fixation at the level of aortic valve annulus. The stability of the connection of the frame-to-calcified aortic valve prevents migration of the prosthesis. Whenever the prosthesis is well fixed, the risk of leakage between stent and the sinotubular junction is significantly reduced, despite the short length of the sinotubular junction.

Apparatuses and methods of the present invention can be used to treat ascending aortic dilatation and concomitant aortic valve stenosis. In these patients, any replacement valve described above can be used in conjunction with the invention. Apparatuses and methods of the present invention can also be used to treat ascending aortic dilatation and concomitant ascending dilatation. In these patients replacement valves that can be affixed infravalvularly and do not necessitate calcification of the aortic valve to be implanted into the patient (such as the JenaValve) are preferably used as part of the invention.

Frame-to-frame connection. The prosthetic valve is coupled to the tubular graft with the novel concept of a frame-to-frame connection.

Individualization. After evaluation of computed tomography scans appropriate size of the prosthetic valve (diameter) and the tubular graft (proximal and distal diameter, lengths of uncovered and covered parts) will be defined. It allows individualization of the prosthesis according to the aortic parameters. The concept of the frame-to-frame connection allows the option of a connection between the valve and the tubular graft to be done in the operating room or the possibility of remote customizing.

Free diastolic blood flow to the coronary arteries. The stent graft in the proximal portion can be uncovered to facilitate the coronary arteries perfusion. The prosthetic valve can be implanted in the position of the diseased valve. It warrants the physiologic diastolic blood flow to the coronary arteries.

Technical device and implantation details. An endoluminal prosthesis comprises a tubular graft, that can be a body portion of a thoracic aortic prosthetic device, having proximal coupled one of the commercial available self-expandable TAVI prosthetic valves. The stent graft in the proximal portion can be uncovered to facilitate the coronary arteries perfusion. The remaining portion of endoluminal prosthesis starting at the level corresponding to the sinotubular junction can be covered.

The aortic valve prosthesis can coupled to the stent graft with clips, sutures such as about 4 to about 6 knots, or other frame-to frame connection done in the operating room or at a remote site after selecting appropriate size of aortic valve prosthesis and stent graft. The stent graft length must be appropriate to cover the entire ascending aorta landing distally short before the innominate artery. For patients with aneurysmal distal ascending aorta and normal aortic arch the prosthesis should be long enough to cover the proximal part of the aortic arch with a scallop for innominate artery orifice. This prosthesis coupled with the prosthetic valve can be put into the deployment device and implanted intraluminal from a remote location in the same manner as described for TAVI-procedure and thoracic stents implantation.

Example. Endovascular Single Stage Wheat Procedure: a CT-Based Feasibility Study Wheat procedure consists of aortic valve and ascending aortic replacement with preservation of the sinus of Valsalva. Purpose of this study was to characterize post-stenotic proximal aortic anatomy and define the design of a single device for endovascular Wheat procedure comprising a percutaneous applicable prosthetic valve coupled to a tubular, with proximal part uncovered, graft.

In the past 5 years, among 1196 patients with severe aortic stenosis screened for transcatheter aortic valve implantation, 79 non-bicuspid, symptomatic patients had ascending aortic diameter >4.5 cm. In those with high-resolution computed tomography angiography diameters of aortic annulus, sino-tubular junction (STJ), distal ascending aorta, distances from coronary artery ostia to aortic annulus and STJ, and aortic curvature lengths were measured.

Altogether, 51 patients (16 females; aged 85±8 years; 19 TAVI, 10 open Wheat procedures, 22 managed conservatively) were included. Required annulus diameter for implantation of currently available valve prostheses was met in 49% (25/51). Novel 32 mm prosthetic valve appropriate for annular range 28-30 mm would extend device applicability to 78% (40/51). In 88% (45/51) of patients the required minimum 10 mm distance between aortic valve annulus and coronary artery ostia was found. Proximal and distal diameters of the graft covered portion ranging between 30-46 mm would enable 10% graft oversizing in all but 6 patients. The median distance between left and right coronary artery ostia and STJ was 2.6±1.5 mm and 3.2±1.7 mm, respectively.

What is claimed:

1. A cardiac repair prosthesis comprising:
    a first radially expandable scaffolding comprising a unidirectional valve configured for implantation into the aortic valve region of a patient; and
    a second radially expandable scaffolding having a size and shape for implantation into the ascending aorta of said patient;
    the first radially expandable scaffolding and the second radially expandable scaffolding being joined by at least one joining element, and,
    at least one portion of the first radially expandable scaffolding having a diameter that is different from a diameter of at least one portion the second radially expandable scaffolding.

2. The cardiac repair prosthesis of claim 1 wherein the at least one joining element comprises a suture.

3. The cardiac repair prosthesis of claim 1, wherein the at least one joining element comprises a clip.

4. The cardiac repair prosthesis of claim 3, wherein the clip has a hinge and locking mechanism.

5. The cardiac repair prosthesis of claim 1, wherein the unidirectional valve comprises one or more leaflets.

6. The cardiac repair prosthesis of claim 1, wherein the unidirectional valve comprises two or three leaflets.

7. The cardiac repair prosthesis of claim 5, wherein the leaflets comprise a biological material.

8. The cardiac repair prosthesis of claim 5, wherein the leaflets comprise a synthetic material.

9. The cardiac repair prosthesis of claim 1, wherein the first radially expandable scaffolding is partially covered by a material that is substantially impervious to blood.

10. The cardiac repair prosthesis of claim 1, wherein the first radially expandable scaffolding is configured for implantation in the aortic annulus of a patient.

11. The cardiac repair prosthesis of claim 1, wherein a longitudinal end of the first radially expandable scaffolding is joined to a longitudinal end of the second radially expandable scaffolding by the at least one joining element.

12. The cardiac repair prosthesis of claim 1, wherein the second radially expandable scaffolding is at least partially covered by a material that is substantially impervious to blood.

13. The cardiac repair prosthesis of claim 1, wherein the second radially expandable scaffolding includes a first longitudinal end and a second longitudinal end, wherein a diameter of the second radially expandable scaffolding at the first longitudinal end is different than a diameter of the second radially expandable scaffolding at the second longitudinal end.

14. The cardiac repair prosthesis according to claim 1, wherein at least a portion of the first radially expandable scaffolding has a diameter that is less than a diameter of at least one portion the second radially expandable scaffolding.

\* \* \* \* \*